United States Patent
Kiehs et al.

[11] 4,012,521
[45] Mar. 15, 1977

[54] FUNGICIDE

[75] Inventors: Karl Kiehs, Lampertheim;
Ernst-Heinrich Pommer,
Limburgerhof, both of Germany

[73] Assignee: Badische Anilin- & Soda-Fabrik Aktiengesellschaft, Ludwigshafen (Rhine), Germany

[22] Filed: May 6, 1970

[21] Appl. No.: 35,264

[30] Foreign Application Priority Data
May 6, 1969  Germany .......................... 1923019

[52] U.S. Cl. .............................. 424/301; 106/15 R
[51] Int. Cl.$^2$ ...................... A01N 9/12; A01N 9/24
[58] Field of Search ........................... 424/308, 301

[56] References Cited
UNITED STATES PATENTS 2,259,869  10/1941  Allen .............................. 424/301 X
2,975,098  3/1961   Driver et al. ...................... 424/301

OTHER PUBLICATIONS

Haerdtl, Chemical Abstracts, 1964, vol. 60, pp. 8374 and 8375.

*Primary Examiner*—Dale R. Ore
*Attorney, Agent, or Firm*—Johnston, Keil, Thompson & Shurtleff

[57] ABSTRACT

A process for controlling fungi with the aid of substituted chloromethylaroyl sulfides, the aryl radical being substituted by various radicals, and fungicides containing these active ingredients.

3 Claims, No Drawings

FUNGICIDE

The present invention relates to fungicides containing chloromethylaroyl sulfides.

It is known to use tetramethylthiuram disulfide and pentachlorophenol as fungicidal active ingredients; however, their action is not satisfactory.

We have now found that chloromethylaroyl sulfides having the formula

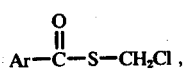

where Ar denotes a naphthyl radical or a phenyl radical which may bear one to five identical or different substituents selected from the group consisting of lower alkyl (methyl, ethyl, n-propyl, isopropyl, sec-butyl, tert-butyl), hydroxy, lower alkoxy (methoxy, ethoxy, isopropoxy, n-propoxy, tert-butoxy), aryl (preferably phenyl or naphthyl; these rings may be substituted by lower alkyl radicals, lower alkoxy radicals, halogen (Cl, Br) or nitro groups), 2-, 3- or 4-pyridyloxy, halogen (fluorine, chlorine, bromine, iodine), halomethyl (trifluoromethyl, trichloromethyl, tribromomethyl, fluorodichloromethyl), nitro, lower alkylmercapto ($CH_3S$, $C_2H_5S$, $t-C_4H_9S$), lower — if desired, chlorosubstituted — alkenylmercapto (preferably allyl, methallyl, 3,3-dichloromethallyl, 2,3,3-trichloroallylmercapto), arylmercapto (preferably phenylmercapto; this phenyl ring may bear one or more lower alkyl radicals or halogen (Cl, Br) atoms as substituents), lower alkyl or allylsulfonyl (e.g. $CH_3—SO_2—$, $C_2H_5SO_2$, $iso-C_3H_7SO_2$, allylsulfonyl), arylsulfonyl (preferably phenylsulfonyl; this ring may be substituted by lower alkyl radicals, lower alkoxy radicals or halogen (Cl, Br)), dialkylamino (dimethylamino, diethylamino), phenylamino, arylsulfamido (e.g. phenylsulfamido, p-tolylsulfamido, p-bromophenylsulfamido), amidosulfonyl (preferably arylated or dialkylated (lower alkyl radicals) on the nitrogen atom; both lower alkyl radicals may together form a ring, as in the case of morpholine or piperidine), lower saturated aliphatic acyl radicals (e.g. acetyl, propionyl), aromatic acyl radicals (preferably benzoyl or naphthoyl; these radicals may be substituted, for example, by alkyl (methyl, ethyl, isopropyl), alkoxy (methoxy, ethoxy), halogen (Cl, Br) or nitro groups), or chloromethylthiocarbonyl radicals, have a good fungicidal action.

The toxicity to warm bloods of the active ingredients is very low. The fungicides have diverse uses and are distinguished by an extremely long-lasting action, e.g. when used for protecting wood, leather, surface coating agents, polymer emulsions, paper, and tanning liquors.

The active ingredients may be prepared by reacting hydroxymethylesters with phosphorus pentachloride in absolute ether.

EXAMPLE 1

Chloromethylbenzoyl sulfide 42 parts of phosphorus pentachloride is covered with a layer of absolute ether. While stirring and cooling with ice, an ethereal solution of 33.6 parts of hydroxymethylbenzoyl sulfide is dripped in and the whole stirred for 2 hours at room temperature. The solution is filtered, the filtrate concentrated at 0.01 mm and a bath temperature of 40° C, the residue taken up in methylene chloride and washed with cold aqueous $NaHCO_3$ solution. The organic phase is dried over $Na_2SO_4$ and distilled 20 parts of chloromethylbenzoyl sulfide having a boiling point at 0.1 mm of 111° to 113° C is obtained.

The following compounds may be prepared in an analogous manner:

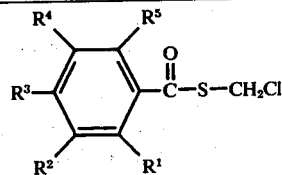

| $R^1$ | $R^2$ | $R^3$ | $R^4$ | $R^5$ | Physical data |
| --- | --- | --- | --- | --- | --- |
| — | — | — | — | — | b.p. (0.1 mm): 111–113° C |
| Cl | — | — | — | — | b.p. (0.1 mm): 112–115° C |
| — | — | Cl | — | — | m.p.: 73–74° C |
| — | — | Br | — | — | m.p.: 78–80° C |
| — | Cl | — | — | — | m.p.: 39–40° C |
| Cl | — | Cl | — | — | b.p. (0.2 mm): 132–134° C |
| — | — | — | Cl | — | m.p.: 76–78° C |
| — | Cl | Cl | — | — | m.p.: 61–63° C |
| — | — | — | — | Cl | m.p.: 51–52° C |
| $C_6H_5SO_2—$ | — | — | — | — | m.p.: 105–107° C |
| Cl | — | — | — | Cl | $n_D^{25}$: 1.6220 |
| Cl | Cl | — | Cl | Cl | m.p.: 90–92° C |
| Cl | Cl | — | Cl | Cl | m.p.: 123–125° C |
| Cl | Cl | Cl | Cl | — | m.p.: 69–71° C |
| — | Br | —COSCH$_2$Cl | — | — | m.p.: 111–113° C |
| — | — | — | — | — | $n_D^{25}$: 1.6444 |
| — | —COSCH$_2$Cl | — | —COSCH$_2$Cl | — | $n_D^{25}$: 1.6440 |
| Cl | — | Cl | Cl | — | m.p.: 62–63° C |
| — | I | Cl | I | — | m.p.: 143–144° C |
| — | — | F | — | — | b.p. (0.4 mm): 97–100° C |
| — | — | $C_6H_5$ | — | — | m.p.: 120–122° C |
| — | — | $CH_3$ | — | — | b.p. (0.1 mm): 110–112° C |

-continued

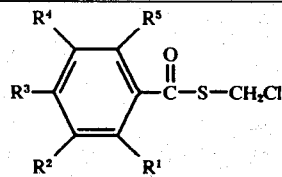

| R¹ | R² | R³ | R⁴ | R⁵ | Physical data |
|---|---|---|---|---|---|
| CH₃ | — | — | — | — | b.p. (0.1 mm): 114–116° C |
| — | CH₃ | — | — | — | b.p. (0.4 mm): 131–134° C |
| — | — | C(CH₃)₃ | — | — | $n_D^{25}$: 1.5730 |
| CH₃ | — | CH₃ | — | — | b.p. (0.1 mm): 113–116° C |
| — | — | CH₃ | CH₃ | — | $n_D^{25}$: 1.5912 b.p. (0.4 mm): 134–136° C |
| — | CH₃O | CH₃O | — | — | m.p.: 89–91° C |
| C₆H₅O | — | — | — | — | $n_D^{25}$: 1.6394 |
| — | NO₂ | — | — | — | $n_D^{25}$: 1.6163 |
| — | CF₃ | — | — | — | b.p. (0.1 mm): 95–97° C |
| Br | — | Br | — | Br | $n_D^{25}$: 1.6713 |
| Cl | — | CH₃O | — | — | b.p. (0.1 mm): 145–148° C |
| — | C₂H₅O | — | — | — | $n_D^{25}$: 1.4945 b.p. (0.5 mm): 145–147° C $n_D^{25}$: 1.6700 |

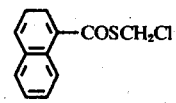

| | SCH₃ | — | — | — | b.p. (0.3 mm): 153–156° C |
| — | S—CH₂—CH=CH₂ | — | — | — | b.p (0.7 mm): 175–177° C |

The agents according to the invention may be used as solutions, emulsions, suspensions or dusts. The form of application depends entirely on the purpose for which the agents are being used; in any case it should ensure a fine distribution of the active ingredient.

For the preparation of solutions to be sprayed direct, hydrocarbons having boiling points higher than 150° C, e.g. tetrahydronaphthalene or alkylated naphthalenes, or organic liquids having boiling points higher than 150° C and having one or more than one functional group, e.g. the keto group, the ether group, the ester group or the amide group, this group or these groups being attached as substituent (s) to a hydrocarbon chain or being a component of a heterocyclic ring, may also be used as spray liquids.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g. polyethylene oxide adducts. Concentrates which are suitable for dilution with water may be prepared from active ingredient, emulsifying or dispersing agent and possibly solvent.

Dusts may be prepared by mixing or grinding the active ingredients with a solid carrier, e.g. kieselguhr, talc, clay or fertilizers.

For the following experiments, the active ingredients in the table below were used:

| No. | formula |
|---|---|
| 1 | 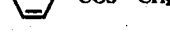 |
| 2 |  |
| 3 | 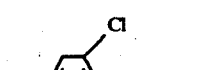 |
| 4 |  |
| 5 | 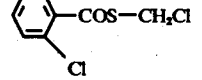 |
| 6 | 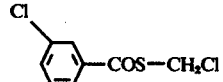 |
| 7 | 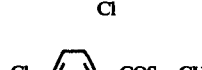 |

-continued

| No. | formula |
|-----|---------|
| 8 | Br—⌬—COS—CH$_2$Cl |
| 9 | CH$_3$—⌬—COS—CH$_2$Cl |
| 10 | ⌬(CH$_3$)—COS—CH$_2$Cl |
| 11 | CH$_3$—⌬(CH$_3$)—COS—CH$_2$Cl |
| 12 | CF$_3$—⌬—COS—CH$_2$Cl |
| 13 | (CH$_3$)$_3$C—⌬—COS—CH$_2$Cl |
| 14 | CH$_3$O—⌬(CH$_3$O)—COS—CH$_2$Cl |
| 15 | ⌬(NO$_2$)—COS—CH$_2$Cl |
| 16 | ⌬(O—C$_6$H$_5$)—COS—CH$_2$Cl |
| 17 | naphthyl—COS—CH$_2$Cl |
| 18 | ⌬(ClCH$_2$SOC)—COS—CH$_2$Cl |

EXAMPLE 2

In the following table, the inhibition values with regard to the fungus Aspergillus niger in nutrient solution are given. The nutrient solutions are inoculated with fungus spores and incubated at 35° C for 120 hours. The extent of the fungus growth is then ascertained.

| Active ingredient no. | Amount of active ingredient in the nutrient solution in parts by weight of active ingredient per million parts of nutrient solution | | | | | | | |
|---|---|---|---|---|---|---|---|---|
| | 100 | 50 | 25 | 10 | 5 | 1 | 0.5 | 0.1 |
| 1 | 0 | 0 | 0 | 0 | 0 | 0 | 0 | 1 |
| 2 | 0 | 0 | 0 | 0 | 0 | 0 | 0 | 1 |
| 3 | 0 | 0 | 0 | 0 | 0 | 0 | 0 | 0 |
| 4 | 0 | 1 | 3 | 3 | 3 | 5 | 5 | 5 |
| 5 | 0 | 0 | 0 | 0 | 0 | 0 | 0 | 1 |
| 6 | 0 | 0 | 0 | 0 | 0 | 0 | 0 | 0 |
| 7 | 0 | 0 | 0 | 0 | 1 | 3 | 5 | 5 |
| 8 | 0 | 0 | 0 | 0 | 0 | 0 | 0 | 0 |
| 9 | 0 | 0 | 0 | 0 | 0 | 1 | 2 | 4 |
| 10 | 0 | 0 | 0 | 0 | 0 | 0 | 0 | 5 |
| 11 | 0 | 3 | 3 | 3 | 3 | 4 | 5 | 5 |
| 12 | 0 | 0 | 0 | 0 | 0 | 0 | 0 | 0 |
| 13 | 0 | 0 | 0 | 1 | 3 | 3 | 4 | 5 |
| 14 | 0 | 0 | 2 | 2 | 3 | 4 | 4 | 5 |
| 15 | 0 | 0 | 0 | 0 | 0 | 0 | 0 | 0 |
| 16 | 0 | 0 | 0 | 0 | 0 | 2 | 3 | 5 |
| 17 | 0 | 0 | 0 | 0 | 1 | 2 | 4 | 5 |
| 18 | 0 | 0 | 0 | 0 | 0 | 1 | 1 | 1 |
| tetra-methylthiuram disulfide (comparative agent) | 1 | 2 | 2 | 4 | 5 | 5 | 5 | 5 |
| control (untreated) | | | | | 5 | | | |

0 = no fungus growth, graduated down to
5 = uninhibited fungus growth

EXAMPLE 3

The active ingredients are dissolved in acetone in amounts of 0.01, 0.005, 0.0025, 0.001, 0.0005, 0.00025 and 0.00012% (by weight, with reference to the agar mixture) and uniformly dispersed in a still liquid malt nutrient agar. The agar is poured into Petri dishes each having a diameter of 9 cm. After the agar has solidified, the dishes are centrally inoculated with mycelium flakes of Coniophora cerebella. The dishes are incubated at 25° C for 8 days, after which period of time the extent of the development of the fungus colony is ascertained.

The figures in the table have the following meanings:
0 = no fungus growth
1 = diameter of the fungus colony of 0.5 to 1 cm
2 = diameter of the fungus colony of 1 to 2 cm
3 = diameter of the fungus colony of 2 to 2.5 cm
4 = diameter of the fungus colony of 2.5 to 4.5 cm
5 = diameter of the fungus colony of 4.5 to 5 cm

| Active ingredient no. | Coniophora cerebella % age active ingredient in the agar | | | | | | |
|---|---|---|---|---|---|---|---|
| | 0.01 | 0.005 | 0.0025 | 0.001 | 0.0005 | 0.00025 | 0.00012 |
| 1 | 0 | 0 | 0 | 0 | 0 | 3 | 3 |
| 2 | 0 | 0 | 0 | 1 | 3 | 4 | 5 |
| 3 | 0 | 0 | 0 | 0 | 0 | 4 | 5 |
| 4 | 0 | 0 | 0 | 1 | 3 | 4 | 5 |
| 6 | 0 | 0 | 1 | 1 | 3 | 4 | 5 |
| 8 | 0 | 0 | 1 | 2 | 3 | 5 | 5 |
| 9 | 0 | 0 | 0 | 1 | 1 | 4 | 5 |
| 10 | 0 | 0 | 0 | 0 | 0 | 0 | 3 |
| 11 | 0 | 1 | 2 | 4 | 4 | 5 | 5 |
| 12 | 0 | 0 | 0 | 0 | 0 | 0 | 1 |
| 13 | 0 | 0 | 0 | 1 | 2 | 4 | 5 |
| 15 | 0 | 0 | 2 | 4 | 4 | 5 | 5 |
| 18 | 0 | 0 | 2 | 3 | 4 | 5 | 5 |
| pentachlorophenol (comparative agent) | 0 | 1 | 3 | 4 | 5 | 5 | 5 |

| Active ingredient no. | Coniophora cerebella % age active ingredient in the agar | | | | | | |
|---|---|---|---|---|---|---|---|
| | 0.01 | 0.005 | 0.0025 | 0.001 | 0.0005 | 0.00025 | 0.00012 |
| control | 5 | | | | | | |

EXAMPLE 4

Pieces of leather measuring 2×2 cm are impregnated with solutions containing 100, 50, 25 and 10 parts of active ingredient per million parts of impregnating solution, placed in glass dishes having a diameter of 5 cm and subsequently sprayed with a suspension of Penicillium glaucum spores. The dishes are incubated at 25° C for 8 days, after which period of time the extent of mold fungus development on the pieces of leather is ascertained.

The figures in the table have the following meanings:
0 = no fungus growth, graduated down to 5 = uninhibited fungus growth.

| Active ingredient no. | Amount of active ingredient in the impregnating solution in parts by weight of active ingredient per million parts of impregnating solution | | | |
|---|---|---|---|---|
| | 100 | 50 | 25 | 10 |
| 1 | 0 | 0 | 0 | 0 |
| 2 | 0 | 0 | 0 | 3 |
| 3 | 0 | 0 | 0 | 3 |
| 10 | 0 | 0 | 0 | 1 |

EXAMPLE 5

60 parts by weight of compound 1 is mixed with 40 parts by weight of N-methyl-α-pyrrolidone. A mixture is obtained which is suitable for application in the form of very fine drops.

EXAMPLE 6

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound 3 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound 4 is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound 5 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 10

3 parts by weight of compound 6 is intimately mixed with 97 parts by weight of particulate kaolin. A dust is obtained containing 3% by weight of the active ingredient.

EXAMPLE 11

30 parts by weight of compound 7 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:
1. A process for controlling fungi which comprises applying to loci to be protected against fungus attack a fungicidally effective amount of a chloromethylaroyl sulfide having the formula

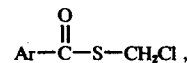

where Ar denotes one of naphthyl, phenyl and phenyl having 1 to 5 identical or different substituents selected from the group consisting of lower alkyl, hydroxy, lower alkoxy, phenoxy, pyridyloxy, halogen, halomethyl, nitro, lower alkylmercapto, lower alkenylmercapto, phenylmercapto, lower alkylsulfonyl, allylsulfonyl, phenylsulfonyl, dimethylamino, diethylamino, phenylamino, phenyl sulfamido, tolyl sulfamido, lower alkyl amidosulfonyl, acetyl, propionyl, benzoyl, naphthoyl and chloromethylthiocarbonyl radicals.

2. A process as claimed in claim 1 wherein said chloromethylaroyl sulfide is one having the formula

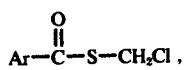

wherein Ar denotes a member selected from the group consisting of phenyl, naphthyl or phenyl substituted by one or more of Cl, Br, I, F, $C_6H_5SO_2$, lower alkyl, lower alkoxy, $C_6H_5O$, $NO_2$, $CF_3$, $SCH_3$, $S-CH_2-CH=CH_2$ and $COS-CH_2Cl$.

3. A process as claimed in claim 1 wherein said chloromethylaroyl sulfide is a member selected from the group consisting of

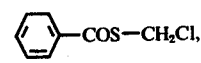

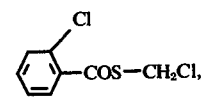

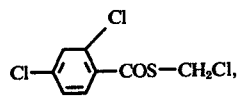

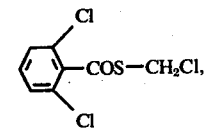

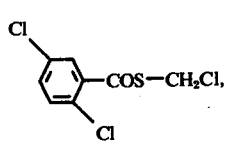

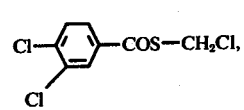

-continued

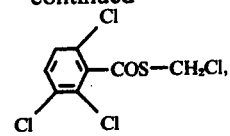

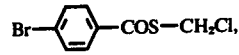

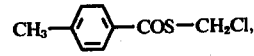

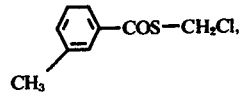

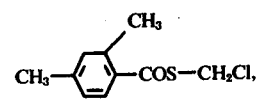

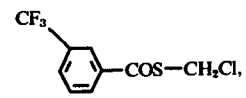

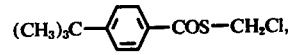

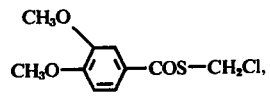

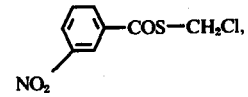

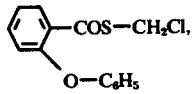

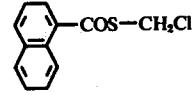

and

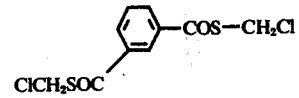

* * * * *